United States Patent
Miller (10) Patent No.: US 9,952,241 B2
(45) Date of Patent: Apr. 24, 2018

(54) METHODS AND APPARATUS FOR ASCERTAINING SPECIMEN AND/OR SAMPLE CONTAINER CHARACTERISTICS WHILE IN TRANSIT

(71) Applicant: Kerry L. Miller, Elkton, MD (US)

(72) Inventor: Kerry L. Miller, Elkton, MD (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 296 days.

(21) Appl. No.: 14/422,903

(22) PCT Filed: Aug. 20, 2013

(86) PCT No.: PCT/US2013/055676
§ 371 (c)(1),
(2) Date: Feb. 20, 2015

(87) PCT Pub. No.: WO2014/031576
PCT Pub. Date: Feb. 27, 2014

(65) Prior Publication Data
US 2015/0241457 A1    Aug. 27, 2015

Related U.S. Application Data

(60) Provisional application No. 61/684,944, filed on Aug. 20, 2012.

(51) Int. Cl.
*G01N 35/00* (2006.01)
*G01N 35/02* (2006.01)
(Continued)

(52) U.S. Cl.
CPC ............. *G01N 35/02* (2013.01); *G01N 21/84* (2013.01); *G01N 35/00732* (2013.01);
(Continued)

(58) Field of Classification Search
CPC .. G01N 21/00; G01N 35/00594; G01N 21/17; G01N 21/0332; G01N 21/31;
(Continued)

(56) References Cited

U.S. PATENT DOCUMENTS

2008/0020481 A1* 1/2008 Yamamoto ....... G01N 35/00594
436/164
2010/0083772 A1* 4/2010 Tanaka ................ G01N 35/026
73/863.91

(Continued)

FOREIGN PATENT DOCUMENTS

EP    2434291 A1    3/2012

OTHER PUBLICATIONS

PCT International Search Report and Written Opinion dated Jan. 3, 2014 (15 Pages).

*Primary Examiner* — Frank Huang (57) ABSTRACT

Methods of identifying a characteristic of a clinical analysis specimen or a sample container containing the specimen are disclosed. The methods include moving the sample container along a track while causing translation and rotation of the sample container, and capturing two or more images of the sample container during the translation and rotation. The track may have one or more moveable belts contacting a carrier to rotate and translate the carrier holding the sample container. Image analysis may be used to read a barcode label of the sample container, determine HIL, and/or physical characteristics of the sample container. Apparatus for carrying out the method are described, as are other aspects.

19 Claims, 7 Drawing Sheets

(51) Int. Cl.
*G01N 21/84* (2006.01)
*G06K 7/10* (2006.01)

(52) U.S. Cl.
CPC ..... *G06K 7/1092* (2013.01); *G01N 2021/845* (2013.01); *G01N 2035/00752* (2013.01); *G01N 2201/062* (2013.01); *G01N 2201/12* (2013.01)

(58) Field of Classification Search
CPC .... G01N 21/59; G01N 33/5302; G01N 33/86; G01N 35/025; G01N 35/02; G01N 35/026; G01N 21/03; G01N 21/78; G01N 35/00732; B01L 3/00; B01L 3/5453
USPC ...... 250/281, 292, 288, 441.11, 442.11, 526; 73/23.2, 23.3, 23.41, 23.42, 28.01, 31.01, 73/31.07, 863, 863.11, 863.02, 863.03, 73/863.12, 863.23, 863.71, 864.33, 432.1
See application file for complete search history.

(56) References Cited

U.S. PATENT DOCUMENTS

2012/0156796 A1* 6/2012 Drechsler ............. G01N 21/03
436/164
2013/0217141 A1* 8/2013 Lenhard ................ B01L 3/5453
436/164

* cited by examiner

METHODS AND APPARATUS FOR ASCERTAINING SPECIMEN AND/OR SAMPLE CONTAINER CHARACTERISTICS WHILE IN TRANSIT

RELATED APPLICATIONS

The present application claims priority from U.S. Provisional Patent Application Ser. No. 61/684,944, filed Aug. 20, 2012, entitled "METHODS AND APPARATUS FOR ASCERTAINING SPECIMEN AND/OR SAMPLE CONTAINER CHARACTERISTICS WHILE IN TRANSIT" which is hereby incorporated herein by reference in its entirety for all purposes.

FIELD

The present invention relates generally to methods and apparatus for determining a characteristic of a specimen container or its contents.

BACKGROUND

A wide variety of automated chemical analyzers are used to analyze patient specimens. These clinical analyzers may conduct assays using reagents to identify one or more analytes in, or characteristics of, a biological liquid such as urine, blood serum or plasma, cerebrospinal liquids, and the like. For convenience and safety reasons, these biological liquids may be contained within sample containers (e.g., sample tubes) that are generally capped.

Improvements in clinical analyzer technology have been accompanied by advances in pre-analytical sample preparation and handling operations such as sample sorting, sample container centrifugation, cap removal, and the like by automated pre-analytical sample preparation systems called Laboratory Automation Systems (LASs). LASs automatically transport biological liquid samples in sample containers to a number of sample processing stations that have been linked together. These LASs may handle a number of different patient specimens contained in standard, barcode-labeled, and evacuated sample containers. The barcode label may contain an accession number that may be correlated to demographic information that may be entered into a hospital's Laboratory Information System (LIS) along with test orders and other desired information. An operator may place the labeled sample containers (e.g., sample tubes) onto the LAS system, which may automatically route the sample containers for pre-analytical operations such as centrifugation, decapping, and aliquot preparation, prior to the specimen being subjected to clinical analysis by one or more analytical stations that may also be linked to, or part of, the LAS.

For certain clinical assays, a serum or plasma portion (obtained from whole blood by centrifugation) may be used. To prevent clotting, an anticoagulant such as citrate or heparin may be added to the blood specimen. After centrifuging and subsequent de-capping, the open sample container (e.g., tube) may be transported to an appropriate clinical analyzer that may extract liquid specimen from the sample container and combine the specimen with one or more reagents in reaction containers (e.g., cuvettes or cups). Analytical measurements may then be performed, using, for example, photometric or fluorometric absorption readings or the like. The measurements allow determination of values from which an amount of analyte related to the health of the patient may be determined using well-known techniques.

Unfortunately, the presence of certain components (e.g., interferents) such as hemolysis (ruptured red blood cells), icterus (excessive bilirubin), and lipemia (high, visible lipid content) (hereinafter "HIL") in the specimen as a result of some preexisting sample condition or processing may adversely affect an accuracy of the analyte measurement obtained from the clinical analyzer.

In some cases, the integrity of the serum or plasma portion of the specimen may affect the interpretation of the results, i.e., the analyte reading of the clinical analyzer. For example, pre-analytical variables in the serum or plasma portion, which are not related to the patient disease state, may cause a different interpretation of the disease condition of the patient. Pre-analytical variables include HIL. Typically, the integrity of the serum or plasma portion of the specimen is visually inspected by a skilled laboratory technician. This may involve a review of the color of the serum or plasma portion of the specimen. A normal serum or plasma portion has a light yellow to light amber color.

A serum or plasma portion containing hemolysis may be quite reddish in color. Interferents may arise, for example, if an excess number of red blood cells are damaged, possibly during venipuncture, centrifugation, or prolonged storage. When red blood cells are injured, they release low density, reddish-colored hemoglobin into the specimen causing a reddish-colored sample that is said to exhibit "hemolysis." The presence of free hemoglobin may be used to measure the degree of hemolysis and, when the hemoglobin concentration exceeds about 20 mg/dl, the hemoglobin may interfere with the colorimetric determination of analytes in the clinical analyzer due to the reddish interferent contained in the specimen.

A sample containing icterus may be dark yellow/brown in color. Such interferents may arise, for example, from an excess of bilirubin, the result of decaying red blood cells being converted in the spleen into bilirubin. Levels of bilirubin above 2-3 mg/dl are visibly yellowish and may, in particular, adversely affect enzyme-based immunoassays. Such a condition is termed bilirubinaemia or icterus.

A sample containing lipemia may be whitish in color. Interferents may arise, for example, as a whitish appearance in serum or plasma portion due to the presence of excess lipids. Such a condition is called lipemia and lipid levels above about 50 mg/dl may interfere with antibody binding in immunoassays and may, accordingly, affect immunoassay results.

Thus, the degree of red color in a serum or plasma portion may correspond to the amount of hemolysis present, the degree of dark yellow/brown color may correspond to the amount of icterus present in the serum or plasma portion of the specimen, and the degree of whitish color may correspond to the amount of lipemia present in the serum or plasma portion of the specimen.

Subsequent to centrifugation, when the red blood cell portion has been separated from the serum or plasma portion, a skilled technician may visually inspect the serum or plasma portion and, if judged to not have a normal light yellow to light amber color, the specimen may be rejected. Otherwise, the specimen will be processed and analyzed as ordered. However, visual inspection is very subjective, labor intensive, and fraught with the possibility of human error. Thus, various methods have been implemented to ascertain whether hemolysis, icterus, and lipemia (these three conditions are frequently called "HIL") are present in a serum or plasma portion of the specimen.

Typically, a laboratory technician will assign a hemolytic index, an icteric index, and a lipemic index to the serum and plasma portion based upon the color. Based upon the value of the hemolytic index, the icteric index, and the lipemic index, the interpretation of the results from the clinical analyzer can be evaluated. Alternately, if the value of one or more of the indexes is too high, the specimen may be rejected without analysis by the clinical analyzer. As mentioned above, visual inspection can be labor intensive and costly. Furthermore, the possibility of human error exists with visual inspection, the results of the visual inspection may be highly subjective and may vary between workers, and one variable could mask or hide other variables. Thus, it is becoming increasingly important to evaluate the integrity of the serum or plasma portion of the specimen without the use of visual inspection by a laboratory technician.

One attempt to solve this problem involves optically viewing the serum or plasma portion of the specimen after the specimen is transferred to one of the cuvettes of the clinical analyzer. Measuring the optical characteristics of the specimen in the clinical analyzer eliminates the need for visual inspection, but utilizes time on the clinical analyzer and, if the integrity of the specimen is determined to be compromised, additional machine time and a machine cycle is wasted. Furthermore, this procedure cannot be used with clinical analyzers that add reagents to the cuvette prior to adding the serum or plasma portion of the specimen.

One challenge in performing spectrophotometric analysis is that the specimens are initially obtained in a variety of types/sizes of primary patient sample collection containers ("sample containers"). These sample containers are usually tubes of varying diameters and lengths. In the case of a patient blood specimen, the liquid is often centrifuged to separate the serum or plasma portion from the cellular phase (e.g., red blood cell portion). Such sample containers may have a patient identification label, varying and unpredictable amounts of the serum or plasma portion, and can contain a varied amount of specimen liquid.

Because of the problems encountered when interferents are contained in specimens to be analyzed, there is an unmet need for methods and apparatus adapted to rapidly determine a presence of such interferents. The method and apparatus should not appreciably adversely affect the speed of obtaining analytical test results and should be deployable early in the processing so that corrective action by laboratory personnel minimizes delays in patient sample analysis. Furthermore, the method and apparatus should be able to be used on labeled sample containers.

SUMMARY

According to a first aspect, a method of determining a characteristic of a sample container or a specimen contained within the sample container is provided. The method includes moving the sample container along a track while causing translation and rotation of the sample container, and capturing two or more images of the sample container during the translation and rotation.

According to another aspect, an identification apparatus is provided. The identification apparatus includes a track adapted to cause translation and rotation of a sample container containing a specimen, and an imaging apparatus adapted to capture two or more images of the sample container during the translation and rotation.

According to a system aspect, an identification system is provided. The identification system includes a carrier adapted to hold a sample container containing a specimen, a track adapted to cause translation and rotation of a sample container containing a clinical analysis specimen, the track having one or more moveable belts, and an imaging apparatus having an image field adapted to capture at least two images of the sample container during the translation and rotation.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

DETAILED DESCRIPTION

In a first broad aspect, embodiments of the present invention provide methods and apparatus for determining a characteristic of a specimen (e.g., the presence of one or more interferents, liquid height, height of the red blood cell portion, and/or height of a serum or plasma portion) and/or physical characteristics of a sample container containing the specimen (e.g., container height, container diameter, cap type, cap color, whether the container contains a cap, or the like). In particular, the characteristic of a specimen and/or characteristics of a sample container are obtained without stopping the sample container as in prior art systems.

Analyzing a specimen's image to determine specimen characteristics takes time, which adds to processing turnaround time. Prior systems stopped the sample container containing the specimen, such as with a gate, so that the barcode may be read. Such sample identification barcodes are used to aid in routing the sample container to correct stations in an automated transport system. In accordance with an aspect of embodiments of the invention, an identification apparatus acquires images in parallel with specimen transportation. While the sample container containing the specimen is moving along a track (e.g., translating), it may also be rotated. The rotation and translation may be simultaneous in some embodiments. An imaging system obtains two or more images of the sample container, such as at different lateral locations, and tracks the sample container including the specimen through the image field. By knowing the approximate speed of the translation, the identification apparatus may correlate all the images that belong to a particular sample container translating through the field of view. Thus, multiple sample containers including the specimens can be present in the image field simultaneously. Each sample container including a specimen may be tracked in parallel via the expected location on the image. The barcodes may be read, on the fly, as the sample container moves across the image field. Additionally, or optionally, one or more characteristics of the specimen may be determined as the sample container moves across the image field. The ability to read barcodes, and/or determine specimen characteristics as the sample traverses across the image field, greatly improves system throughput and efficiency, as the sample container does not have to stop moving.

The method may be carried out as a pre-analysis step prior to the liquid sample (specimen) being presented to a clinical analyzer for analytical analysis. In particular, embodiments according to one aspect of the present invention may provide for rapid pre-inspection for a presence of an interferent. This aspect is accomplished by subjecting a blood specimen to an appropriate centrifugation to separate the specimen into a red blood cell portion and a blood serum or plasma portion, and then testing for the presence of an interferent, such as hemolysis, icterus, and/or lipemia (hereinafter "HIL"), or other liquid non-uniformities therein (e.g., improper specimen level). If the specimen is found to be acceptably free of interferents, it is allowed to continue to be routinely processed for analytical analysis.

In one aspect, if the specimen is found to contain more than a predefined amount of lipemia, then the sample may be rejected. The lipemic sample may then be subjected to a special pre-processing operation adapted to reduce an amount of lipemia therein. The specimen may then be allowed to be routinely processed for analysis or possibly retested for the presence of an interferent. In another aspect, if the specimen is found to contain more than a predefined amount of hemolysis, then the sample may be allowed to continue and be routinely processed for analytical analysis. However, the extent or degree of hemolysis may be reported along with the analytical results. Alternatively, the hemolyzed specimen may be subjected to a more sophisticated determination of the amount of hemolysis so that any analytical tests to be conducted on the specimen that are not affected by the presence of hemolysis may be routinely completed, and possibly a redraw of a fresh specimen may be ordered and undertaken. If the specimen is found to contain more than a predefined amount of icterus, then the specimen may be allowed to be routinely processed for analytical analysis and the extent or degree of icteria may be reported along with the analytical results.

These and other aspects and features of the invention will be described with reference to FIGS. 1A-6 herein.

Figure 1A:
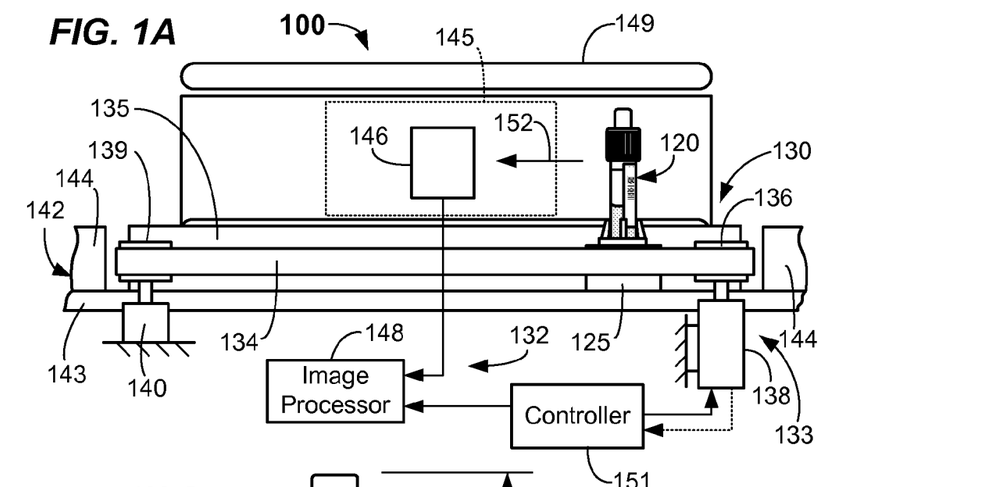
FIG. 1A illustrates a side plan view of an identification apparatus according to embodiments.

FIG. 1A illustrates an identification apparatus 100 capable of automatically determining a characteristic of a sample container 120 (e.g., test tubes or blood collection tubes—see FIG. 1B) and/or characteristic of a specimen 120S contained in the sample container 120. This may be performed prior to analysis by a clinical analyzer. Any generally clear or transparent container may be used, such as a sample cup, cuvette, or other clear glass or plastic container.

Figure 1B:
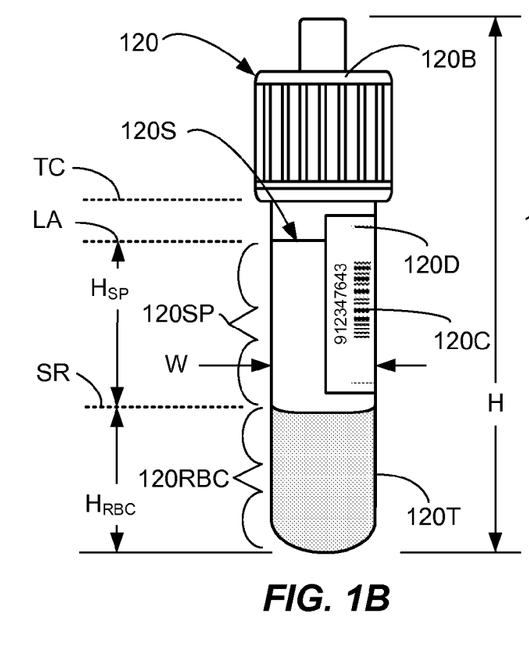
FIG. 1B illustrates an enlarged side plan view of a sample container having a cap and containing a centrifuged specimen according to embodiments.
Figure 1C:
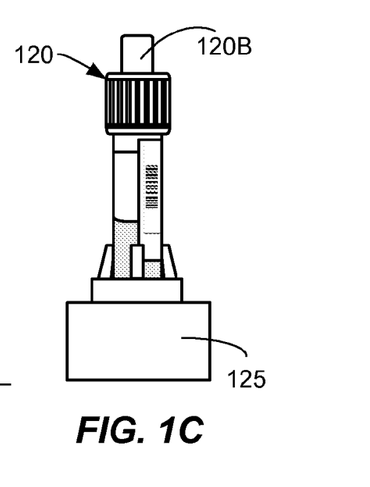
FIG. 1C illustrates a side plan view of a sample container held in a carrier according to embodiments.

Typically, the specimen 120S (hereinafter "specimen") to be automatically processed may be provided to the identification apparatus 100 in the sample containers 120, which may be capped with a cap 120B. The cap 120B may be of various different shapes and colors. Each of the sample containers 120 (e.g., sample tubes) may be provided with identification indicia and/or information 120C, such as a barcode, alphabetic, numeric, or alphanumeric indicia, that may be readable. The indicia and/or information 120C may indicate a patient's identification as well as the assay procedures to be accomplished upon the clinical analysis specimen 120S therein, for example. Such indicia and/or information 120C may be generally provided on a label 120D adhered to, or otherwise provided on the side of, the sample container 120. Such labels 120D generally do not extend all the way around the sample container 120. Accordingly, a window is provided along a side of the sample container 120 where the label 120D is not located and the specimen 120S may be viewed from the side in or through this window without interference by the label 120D. As shown in FIGS. 1A and 1C, the sample containers 120 may be held in carriers 125 that may have additional identification indicia thereon, and which may be moveable along the LAS.

Identification apparatus 100 includes a track 130 adapted to cause translation and rotation of the sample container 120 containing a specimen 120S, and an imaging apparatus 132 adapted to capture two or more images of the sample container 120 during the translation and rotation. The track 130 may be of any suitable construction that causes transport of the sample container 120 while causing translation and rotation. In one embodiment, the track 130 includes a drive apparatus 133 (FIG. 1A). The drive apparatus 133 may have a first moving member such as a first moving belt 134 that contacts the carrier 125 holding the sample container 120. In the embodiment shown in FIGS. 1A and 1D, the first moving belt 134 contacts a first side of the carrier 125 and a stationary wall 135 contacts a second side opposite the first side. The stationary wall 135 may be coated in any suitable manner to provide a high-friction surface. The first moving belt 134 may be driven by a drive pulley 136 that may be driven by a drive motor 138 and may be supported along its length by one or more idler pulleys 139. The one or more idler pulleys 139 may be supported by a rotational support 140, such as a suitable bearing or bushing. The belt 134 may be any suitable elastomer belt that may have a high-friction surface. In operation, the carrier 125 containing the sample container 120 is fed to the identification apparatus 100 by a conveyor 142. Conveyor 142 may be any suitable conveyor adapted to convey carriers 125 and may include a moving floor 143 and may include side walls 144. The moving floor 143 may be moving at a speed of about 175 mm/s for example. Other speeds may be used. The first moving belt 134 contacts a first side of the carrier 125 holding the sample container 120. A second side of the carrier 125 opposite the first side may contact the stationary wall 135.

Figure 1D:
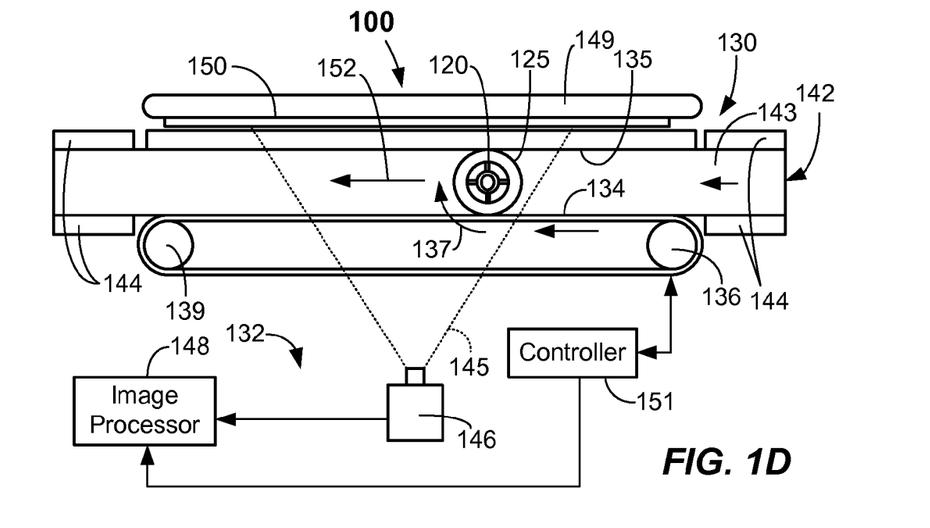
FIG. 1D illustrates a top plan view of an identification apparatus according to embodiments.

In the configuration shown in FIGS. 1A and 1D, the sample container 120 containing the specimen 120S may rotate as it travels (e.g., translates) in front of the imaging apparatus 132. The imaging apparatus 132 includes a camera 146 and an image processor 148. A suitable camera is a model Dragonfly2 (DR2) available from Point Grey Research. Other digital cameras may be used. The image processor 148 may be any suitable device that is capable of performing an analysis of the captured images. For example, the image processor 148 may be a computer having a suitable processor such as a microprocessor-based central processing unit (CPU) and memory and may perform the analysis and tracking of the sample container 120 as it travels on the track 130. The image processor 148 is adapted to analyze the two or more images in some embodiments. An illumination source 149 may be used to illuminate the sample container 120 on the track 130. The illumination source 149 may be one or more LED lights, for example. Other types of lighting may be used. The imaging apparatus 132 may also include an imaging background 150, wherein the sample container 125 is located between a camera 146 of imaging apparatus 132 and the imaging background 150. The imaging background 150 may be black and may be about 150 mm×1200 mm in area, for example. Other colors and sizes for the imaging background 150 may be used.

Two or more images are taken as the sample container 120 moves (e.g., translates) across a field of view (designated by dotted lines 145) of the camera 146. The field of view 145 of the camera 146 may have a size that is large enough to capture multiple images of the sample container 120 as it passes by. In some embodiments, two or more images may be taken as the sample container 120 moves across the field of view 145. In other embodiments, three or more, four or more, five or more, six or more, seven or more, eight or more, or even more images may be taken within the field of view 145. Each respective image that is captured by the imaging apparatus 132 may be saved separately and correlated with information received from the controller 151 to correlate the image of the sample container 120 with other images based upon an expected location change in subsequent images. The image processor 148 may select certain ones of the plurality of images and perform an analysis thereof. Optionally, the analysis may simply use the known operational speed to track the lateral location of the sample container 120 in the images.

As a result, according to one or more embodiments, the sample container 120 does not have to stop for the images to be acquired. Once acquired, the image analysis software of the image processor 148 manages the images in order to track and separate the various images so that one or more of the images can be analyzed. The image processor 148 may receive information about the speed of travel of the belt 134 from the controller 151 in some embodiments. The controller 151 may be adapted to control a rotational speed of the belt 134. The speed of the belt 134 determines the speed of rotation of the carrier 125 and, thus, the speed of rotation of the sample container 120. The speed of the belt 134 also controls the translation speed of the carrier 125 along the direction of travel (designated by arrow 152). In the depicted embodiment, the drive system 133 of the identification apparatus 100 is configured so that it causes simultaneous translation and rotation of the carrier 125 and, thus, the sample container 120. In other words, the rotation of the carrier 125 and, thus, the sample container 120 as indicated by arrow 137, may be simultaneous with the translational motion of the carrier 125 and, thus, the sample container 120 as indicated by arrow 152.

Figure 2A:
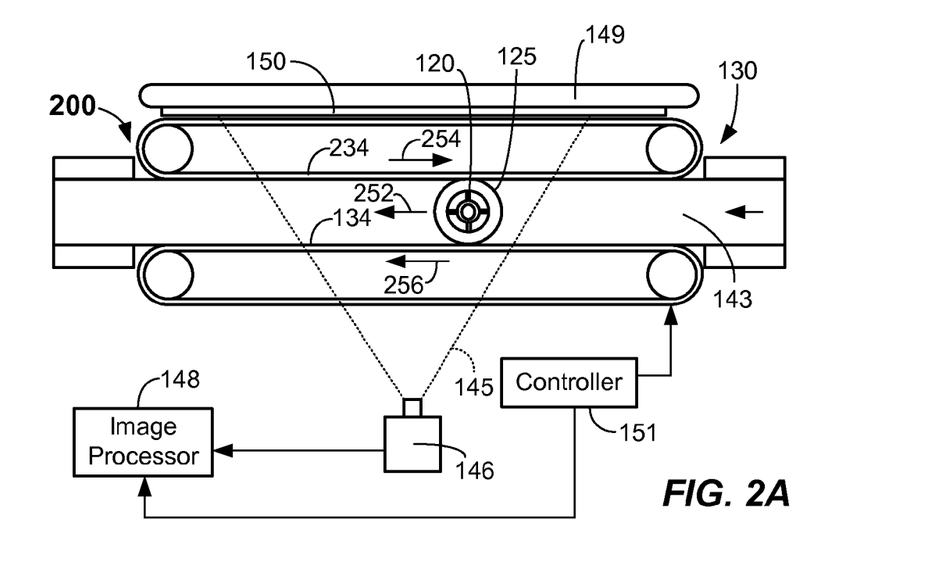
FIG. 2A illustrates a top plan view of an alternative identification apparatus having two moving belts according to embodiments.

FIG. 2A illustrates an alternative embodiment of the identification apparatus 200. In this embodiment, a second belt 234 is added to the identification apparatus 200. The second belt 234 is arranged to be across from the first belt 134, such as across the moving floor 143. The second belt 234 is configured and adapted to contact a second side of the carrier 125 holding the sample container 120, wherein the second side is positioned opposite from the first side. With this configuration, many possibilities for combinations of rotation and translation of the carrier 125 and, thus, the sample container 120 across the field of view 145 may be provided. For example, in a first embodiment as shown in FIG. 2A, the carrier 120 holding the sample container 120 may be contacted with the two moving belts 134, 234, and the directions of the respective belts 134, 234 may be opposite as indicated by arrows 254, 256.

Figure 2B:
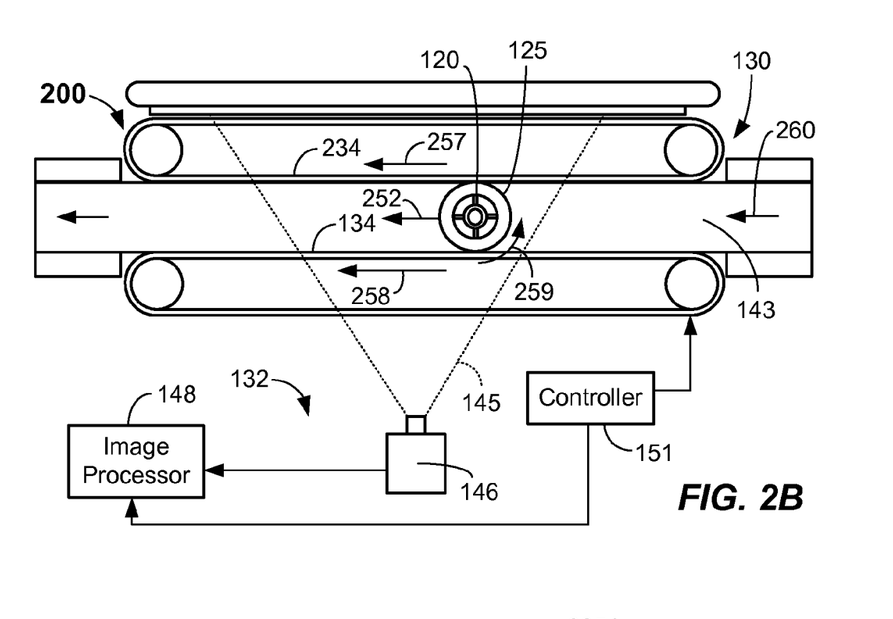
FIG. 2B illustrates a top plan view of an identification apparatus having two moving belts and provides another operational mode according to embodiments.
Figure 3A:
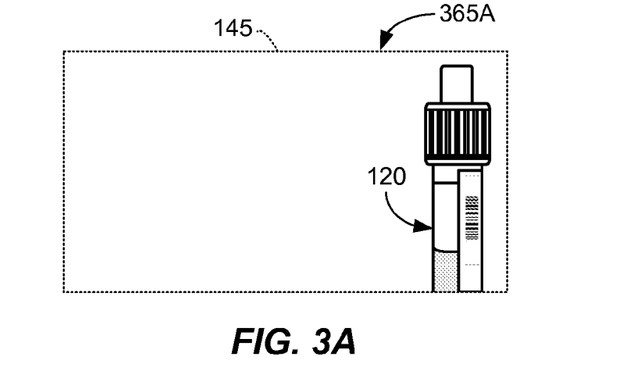
FIGS. 3A-3D illustrate representative images of a sample container at various lateral locations in a field of view of the image according to embodiments.
Figure 3B:
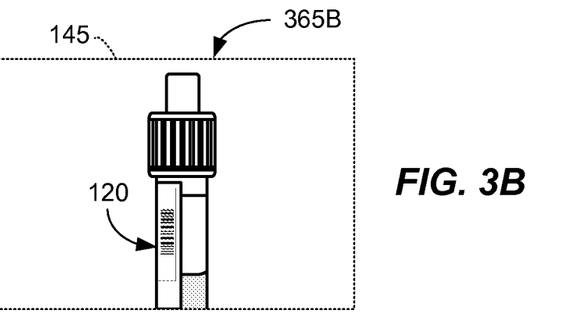
Figure 3C:
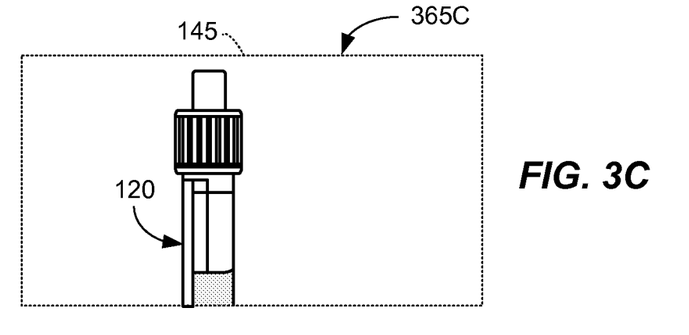
Figure 3D:
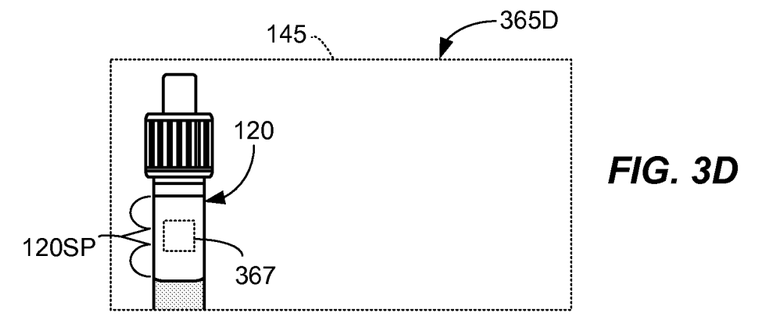

In other embodiments, one of the belts 134 or 234 may be stopped while the other continues to move, thereby performing in the manner discussed above for the single belt version of FIGS. 1A and 1D. In other embodiments, the two belts 134, 234 may be driven at the same speed but different directions. In yet other embodiments, the two moving belts 134, 234 may be moving in a same direction but at different speeds as is shown in FIG. 2B. Thus, the rotation 259 may be accomplished and the speed of translation 252 may be sped up, or slowed down, relative to the speed of the moving floor 143 designated by arrow 260. Thus, a desired rotational speed (e.g., rotation rate) may be achieved together with any desired translational speed as the sample container 120 moves through the field of view 145. The rotation may be one full rotation (e.g., about 360 degrees) within the field of view 145 or as needed to obtain the desired information (e.g., barcode, physical analysis of the sample container 120, or characteristic of the specimen 120S).

In yet other embodiments, the belts 134, 234 may be controlled in order to solely translate the carrier 125 holding the sample container 120 at certain times, solely rotate the carrier 125 at certain times, and both rotate and translate the carrier 125 at other times. Thus, for example, as the image analysis finds a selected image and determines that the label 120D is oriented to the back, the rotation may be momentarily stopped in order to perform any one or more of the HIL analyses. For example, the rotation may be stopped momentarily by moving the belts 134, 234 at a same speed.

In the embodiments described herein, the image processor 148 may analyze at least one of the two or more images to determine a characteristic of the sample container 120 or of the specimen 120S contained in the sample container 120. For example, in one or more embodiments, the image processor 148 may analyze at least one of the two or more images to read a barcode provided on the sample container 120, such as a barcode 120C on the barcode label 120D (FIG. 1B). According to this embodiment, each of the digital images captured by the digital camera 146 may be fed to suitable software operating in the image processor 148, such as barcode recognition software. There are a number of commercially-available and open source software libraries that support reading a barcode from an image, such as ZBar, BarBara, and ZXing, for example. Other libraries may be used. Fundamentally, they operate by searching for the visual characteristics of barcodes in the image and then, once isolated, apply the various algorithms that define particular barcode symbologies. When a decoding is successful the software returns a value. Some software implementations might also provide additional detail, such as a reading strength (score) and the image area and location that was used to decode the barcode 120C.

Any tracked sample container 120 will have multiple images of the sample container 120 extracted from the overall image. This collection of images (e.g., 365A-365D, FIGS. 3A-3D, respectively) from a single sample container 120 traversing through the field of view 145 of the camera 146 has different views of sample container 120 as it rotates and translates. In one embodiment, all images in the collection would be processed by the barcode reading library software. In this way it will be known what views show a decodable barcode and what views do not. Having multiple views with a matching barcode decode increases confidence in the barcode read. This attribute or feature can also help classify what images are likely to be of interest for viewing the sample container contents. Other features such as the vertical edge of a barcode label 120D are also useful for isolating the potential view of the contents.

Once the images have been parsed, any extracted barcode information may be stored in memory and used to relate to the specimen location, when the identification apparatus 100 is used as part of a larger clinical analysis system. In some embodiments, the processing may stop as soon as a sufficient amount of the barcode is available in the image at a particular rotational orientation. Optionally, additional images may be analyzed and read to verify the information. For example, in some embodiments all of the images may be analyzed by the barcode-reading software. In other embodiments, two or more, three or more, or even four or more images from the image field 145 may be analyzed to verify and improve the confidence level in the read information from the barcode.

FIGS. 3A-3D illustrate several images 365A-365D taken as the sample container 120 travels across the image field 145 (e.g., from right to left) under the action of the one or more belts 134, 234. As can be seen, four images are taken across the field of view in the example. More or less images may be taken. For example, the number of images per each field of view may be two or more, three or more, four or more, five or more, six or more, seven or more, eight or more, or even a larger number of images per image field 145. As can be seen, parts of the barcode may be read in the first and second images 365A, 365B. Thus, the barcode recognition software may read the barcode and the read barcode information may be stored and/or used to engage with the LAS and/or LIS such that the location of the sample container 120 and processing status is known. For each image, a blob analysis may be performed looking at differences in digital counts from the imaging background 150. Using a black uncluttered imaging background 150 makes image recognition quite easy, especially with illumination provided on the sample container 120 by the illumination source 149.

From this, the blob analysis may obtain an X and a Y coordinate for the center of the sample container 120 for that image frame 145. In the next captured image, the sample container 120 has moved in the X direction by a certain distance. The analysis software may determine, based upon known speeds of the one or more belts 134, 234, input from the controller 151, or input or information concerning the known speed of the drive motor, if the image is of the same, as the center of the blob should fall within pre-calculated lateral (X) bounds based upon the belt speed and the number of frames captured per second, i.e., the capture rate. The capture rate may be about 30 frames per second, for example. Other rates may be used. In this manner, if more than one sample container image is contained in a particular image frame 145, the software can easily distinguish and track them from frame-to-frame across the image field 145 based upon expected location.

In yet another aspect, the image processor 148 may analyze at least one of the two or more digital images to determine a characteristic of the sample container 120. For example, a height H (FIG. 1B) may be determined to the top of the cap 120B if capped or the top of the tube body 120T of the sample container 120 if uncapped. This height determination may be performed by identifying the vertical-most pixel in the blob analysis and then relating that to the height H of the sample container 120 based upon the calibration of the camera 146, where any number of pixels in the image equates to a known height. Blob analysis may be used to determine whether the cap 120B is present or not via performing pattern recognition once the mask is created. Likewise, once the mask is created, the blob analysis may determine a width W (FIG. 1B) of the sample container 120 by measuring the pixels between the left-most and right-most pixels of the blob at a predetermined vertical height in the image window 145. Thus, one or more characteristics (e.g., physical dimensions or capped conditions) of the sample container 120 may be obtained without stopping the sample container 120.

In another aspect, a color of the cap 120B may be determined by the imaging analysis taking place in the image processor 148. For example, once the presence of a cap 120B has been determined based upon the pattern recognition, an RGB analysis may be carried out on a predetermined-sized pixel space at a predetermined vertical height in the image 365A-365D based upon the size of the sample container 120 and the shape of the cap 120B. The RGB analysis will measure red (R), green (G), and blue (B) hue values and compare them against predetermined threshold value ranges. Thus, sample containers 120 having caps 120B that are light blue, red, lavender, green, black, royal blue, brown, or pink colors may be determined. Other colors may be determined. The thresholds may be based upon one or more of the R, G, and B values. Thus, R, G, and/or B values may be determined for the pixel space, compared to the thresholds, and a determination of the cap color may be made. This may be cross referenced with the barcode information and the LIS and/or LAS to ensure the correct tests are being performed or identify possible problems, such as the wrong sample container being used.

In another embodiment, the imaging apparatus 132 may be used to determine certain physical dimensional characteristics of the specimen 120S. For example, as represented in FIG. 1B, the liquid-air interface LA, location of the interface SR between the red blood cell portion 120RBC and the serum or plasma portion 120SP, a height of the red blood cell portion $H_{RBC}$, and a height of the serum plasma portion $H_{SP}$, as shown in FIG. 1B may be determined. Once the label 120D is determined to be in back of the sample container 120 (See FIG. 3D) via using pattern recognition, the red blood cell portion $H_{RBC}$ and the height of the serum plasma portion $H_{SP}$ may be determined on the image based upon blob analysis with different count settings for the red blood cell portion 120RBC and the serum plasma portion 120SP. Thus, if there is insufficient sample volume, this may be readily determined.

According to another embodiment, the identification apparatus 100, 200 may be used to automatically determine a presence of one or more interferents (e.g., hemolysis (H), icterus (I), and/or lipemia (L)) in a serum or plasma portion 120SP of a specimen 120S contained in the sample container 120. The presence of the interferent may be detected by the imaging apparatus 132 prior to being further tested by a clinical analyzer, wherein the clinical analyzer may be located at another location along a conveyor 142 of an automated transport system (not shown). In this manner, if the specimen 120S includes an interferent, additional processing, discarding, or a redraw may take place and wasted time on the clinical analyzer may be avoided.

According to one broad aspect, the presence of lipemia may be detected in a centrifuged specimen. Lipemia is a specific sample quality discoloration defect, which may be resolved with special processing before the specimen 120S is tested or analyzed on an analytical instrument. The definition of lipemia (also spelled lipaemia) is the abnormally high presence of lipids (fats) in the blood. Lipids exist as small particles not soluble in water. Typically, the serum or plasma portion 120SP (FIG. 1B) is relatively clear. In a lipemic sample, however, the serum or plasma portion 120SP of centrifuged blood may appear to be white or milky in color due to the presence of the lipids. A common cause of lipemia is eating fatty foods. After the lab is aware the sample is lipemic, they may further process the specimen 120S to remove or reduce the lipids. For example, they may introduce a solvent or other material to reduce the amount of lipemia. Once this is complete, the specimen 120S can be properly analyzed by the clinical analyzer instrument and the lab will be relatively more confident of the test results.

According to embodiments, lipemia may be detected by embodiments of the invention by the identification apparatus 100, 200 after centrifugation of the specimen 120S. By detecting lipemia at that point in the process, the specimen 120S may not be wasted, erroneous test results may be prevented, and the patient test result delay may be minimized. Because the specimen 120S may be screened for interfering levels of lipemia, a technician or user may be alerted via a screen warning, warning bell, etc. if the levels are above predetermined limits. The sample container 120 may then be routed to a place where user corrective action or additional processing may take place. After the specimen 120S is corrected or additionally processed, it can be provided to an analytical instrument for analysis.

To determine a presence of lipemia in the serum or plasma portion 120SP of the specimen 120S, an image 365D (e.g., a digital image, FIG. 3D) of the serum or plasma portion 120SP is obtained, such as with the camera 146. This image 365D may be processed by the image processor 148. For example, the analysis carried out by the processor 148 may involve the detection of lipids as an interferent, for example. The presence of lipids may be determined by performing a blob analysis on the image 365D. The image 365D containing the label 120D rotated to the rear is extracted by pattern recognition (see FIG. 3D), and then the serum or plasma portion 120SP may be isolated within the image 365D based upon locating the serum and red blood cell interface SR and the liquid air interface LA by edge detection coupled with feature extraction and analysis. An RBG analysis of a smaller region 367 at the center of this isolated region of the serum or plasma portion 120SP may then be performed. For example, RGB values may be obtained of the smaller region 367 of the image 365D and then compared against predetermined limits. Limits may be based upon R, G, and B values, just R and B values, just R and G values, or just G and B values, for example. Other color analysis may be performed such as RBGY. Other types of color analysis may be performed. The various predetermined hue limits may be set based upon experimentation, by reading RGB values for various levels of lipemia in experimental specimens, and setting range limits for any suitable combination of the R, G, and/or B values. When the image processor 148 successfully detects that a sample is lipemic, then that specimen 120S may not be immediately analyzed, and may be rerouted to another area on the analyzer instrument or automation system that is reserved for lipemic sample pre-processing. A lipemic index value may be determined and assigned. The lab technician may then perform pre-processing activities and then insert the specimen 120S on an analyzer instrument or LAS.

According to another broad aspect, embodiments of the invention are directed at methods and apparatus that may be used to detect a hemolyzed specimen 120S contained in a sample container 120 of centrifuged blood. The method, similar to the method disclosed for lipemic analysis, includes capturing multiple images as the sample container 120 translates and rotates across the field of view 145, isolating an image (e.g., 365D, FIG. 3D) with the label oriented to the rear and then performing an analysis of that digital image to isolate the serum and plasma portion 120SP. Color analysis may then be performed on a representative portion (e.g., smaller portion 367) of the serum or plasma portion 120SP to measure R, G, and B values for the smaller portion 367. Hemolysis is a sample quality discoloration issue, and it cannot be resolved with special processing. Hemolysis (also spelled haemolysis) may occur when the red blood cells rupture and the hemoglobin inside is released into the serum or plasma portion 120SP of the centrifuged blood specimen 120S, thus giving the serum or plasma section 120SP a more reddish color or appearance. Along with a more reddish color, potassium may be released into the serum or plasma portion 120SP, which may give erroneous results when tested on an analytical instrument. Incorrect blood collection, handling, storage, and/or processing may cause hemolysis. In the case that a specimen 120S is determined to be containing hemolysis, the usual procedure is to redraw another specimen 120S from the patient. Accordingly, the hemolysis determination by the identification apparatus 100 and method may allow a rapid redraw. In another aspect, detecting the presence of hemolysis in the specimen 120S saves the analytical instrument(s) from performing analytical testing on a specimen 120S whose results may be suspect.

When the serum or plasma portion 120SP of the specimen 120S is imaged and analyzed for lipemia, the RGB values previously obtained and stored in memory may also be used to analyze the color of the serum or plasma portion 120SP in order to make a basic assessment for hemolysis. This assessment may be solely performed or may be performed in conjunction with the lipemic analysis. In the assessment for hemolysis, the region of interest, where there is no label 120D, may have already been found via the earlier search, such as when analyzing for potential lipemia. As for lipemia, predetermined ranges for R, G, and/or B may be set and used to assess the degree of hemolysis. The predetermined ranges for R, G, and/or B may be set based upon experiments conducted for specimens having various degrees of hemolysis. Hemolysis values may be assigned based upon the RGB readings. If the image processor 148 detects that a specimen 120S is hemolyzed, then that specimen 120S may be discarded, an alert may be displayed or sounded or otherwise communicated to alert personnel (e.g., technician) for further evaluation and/or decision making. In other embodiments, the specimen 120S may be sent on to an analytical instrument (e.g., a specialized clinical analyzer) where a precise level of hemolysis can be measured and characterized. Analytical instruments are much better at determining levels of hemolysis and often have rules that determine the exact concentrations of hemoglobin that affect assay results for the various assays ordered for the specimen. As a result, some test results can be reported before the specimen redraw and retesting occurs.

In more detail, a red, green, blue (RGB) system of color analysis may be employed to characterize hemolysis. Accordingly, the camera 146 is adapted to capture images that contain the discernible RGB hues. The respective red (R) hue may be measured on a scale from 1 to a maximum number (e.g., 1-256). Any specimen 120S, which may include a red hue above a threshold value, as established by calibrating with the reference sample 120R, may be determined to be a hemolyzed sample. Optionally, more than one color may be measured and thresholds may be set based upon more than one detected color (e.g., RGB). Image analysis by the image processor 148 may include measuring the color of the serum or plasma portion 120SP in an area 367 located vertically between the liquid-air interface LA and the interface SR, and roughly centered. Based upon the detected hue or hues, a hemolytic index may be determined and reported, and/or otherwise conveyed to the LIS.

According to another broad aspect, the invention is directed at a method and apparatus that may be used to detect icterus in a specimen 120S. An icterus interferent may arise, for example, from an excess of bilirubin, the result of decaying red blood cells being converted in the spleen into bilirubin. Levels of bilirubin above 2-3 mg/dl are generally visibly yellowish or brownish in color and may, in particular, adversely affect enzyme-based immunoassays. Such a condition is also termed bilirubinaemia. The icterus detection method and apparatus is similar to that for detecting hemolysis and lipemia. The method may first rotate and translate the sample container 120 across the image field 145 and capture multiple images. Next, the method may isolate one image as having an orientation acceptable for icterus detection, i.e., with the label 120D rotated to the rear (e.g., image 365D, FIG. 3D). The image processor 148 may then perform an analysis of the captured image for the presence of icterus. According to the method, the same digital image that was taken for the hemolysis and/or lipemia detection may optionally be used for icterus detection. In this case, the image may be analyzed for the presence of a yellow and/or brown color in the smaller central portion 367. Again this may be accomplished via measuring, with the camera 146 (e.g., a digital camera having RGB capability), a degree of yellow and/or brown present in the serum or plasma portion 120SP of the specimen 120S. Threshold range values for each of yellow and/or brown may be experimentally determined and set and may be used to determine and provide an icteric index. For example, a range from 1 to 4 may be employed. Other suitable icteric index values may be used. The central smaller portion 367 of the serum or plasma portion 120SP may be located via the image analysis technique described herein for determining the location of interfaces LA and SR.

Figure 4:
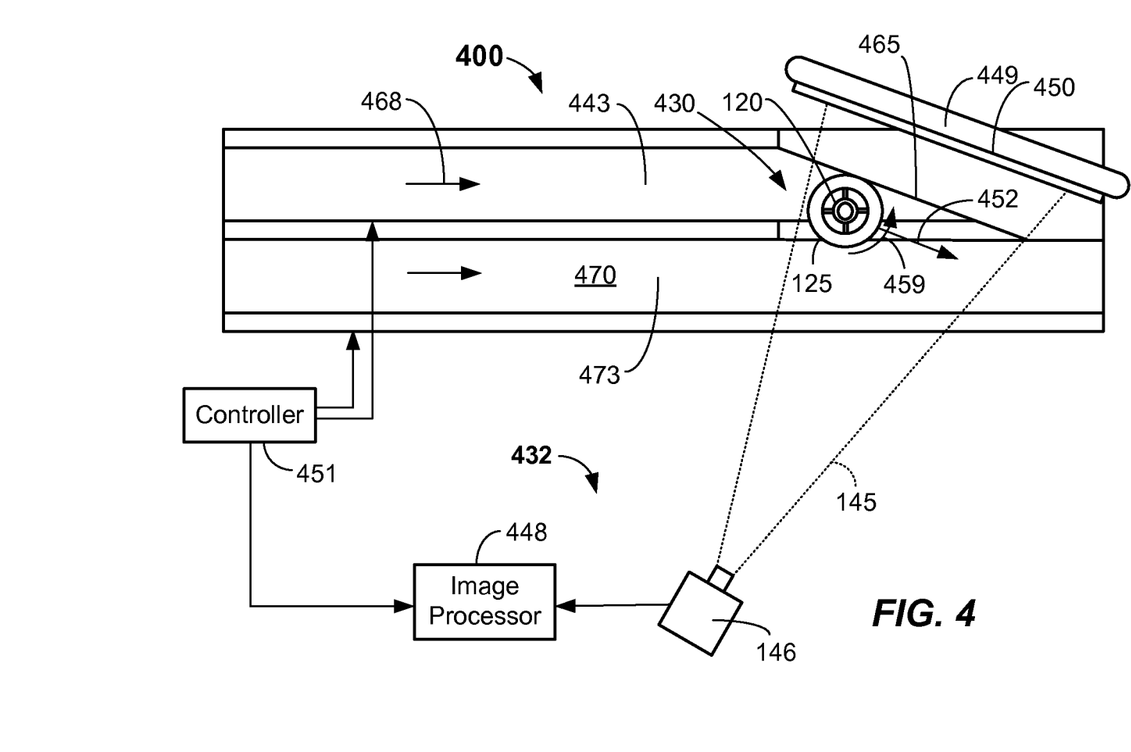
FIG. 4 illustrates a top plan view of an alternate identification apparatus according to embodiments.

Another embodiment of an identification apparatus 400 is shown in FIG. 4. The identification apparatus 400 includes a track 430 and an imaging apparatus 432. In this embodiment, the track 430 includes a stationary wall 465 that is angled relative to a direction of travel of a moving floor 443 as indicated by arrow 468. As the motion of the floor 443 brings the carrier 125 into contact with the stationary wall 465 of the track 430, this contact and friction causes translation along the direction of arrow 452 and rotation of a sample container 120 containing a specimen in the direction indicated by rotational arrow 459. The imaging apparatus 432 is adapted and operational to capture two or more images of the sample container 120 during the translation and rotation, in the manner prescribed in previous embodiments. The imaging apparatus 432, as in previous embodiments, may include an illumination source 449 and an imaging background 450 (e.g., a black planar surface). The identification apparatus 400 may function to read a barcode on the sample container 120 as the carrier 125 holding the sample container 120 moves from the first track 430 to a second track 470. Optionally, other characteristics of the specimen or the sample container 120 may be obtained through the image analysis as described above. A controller 451 may be used to control a speed of the moving floors 443, 473. As described above, that speed information for at least the moving floor 443 is correlated to the rotational speed and translational speed of the carrier 125 and, thus, may be provided to the image processor 448 to assist in identifying the location of the sample container 120 in the two or more images that are captured by the camera 146 according to the method as the sample container 120 moves across the field of view 145.

Figure 5:
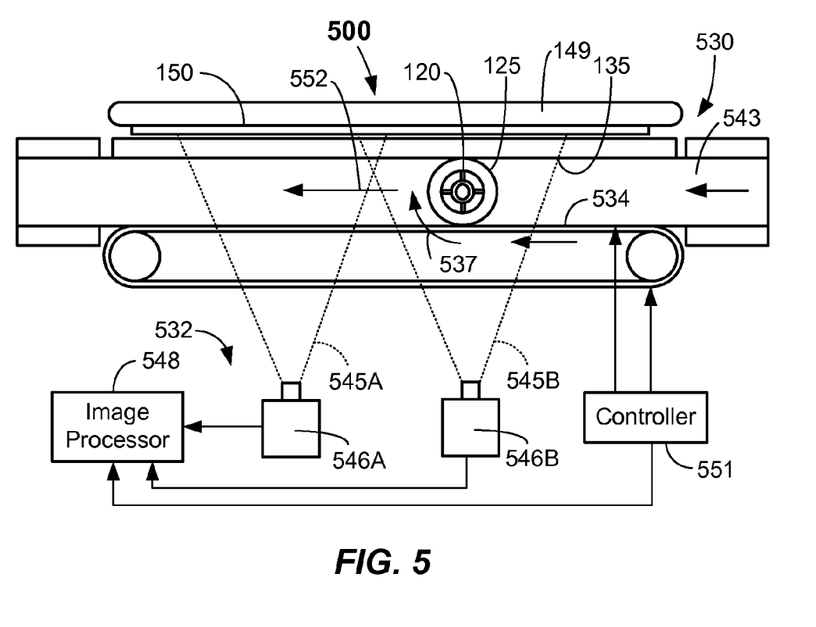
FIG. 5 illustrates a top plan view of an alternate identification apparatus having an imaging apparatus with multiple cameras according to embodiments.

FIG. 5 illustrates another embodiment of an identification apparatus 500. The identification apparatus 500 includes a track 530 and an imaging apparatus 532. In this embodiment, the imaging apparatus 532 comprises two cameras 546A, 546B adapted and operational to capture two or more images of the sample container 120 as the carrier 125 undergoes the translation (as indicated by arrow 552) and rotation (as indicated by arrow 537) in the manner prescribed in previous embodiments. In this manner, the imaging apparatus 532 provides a larger field of view with the individual fields of view 545A, 545B. The fields of view 545A, 545B of each camera 546A, 546B, respectively, may overlap by some amount. The tracking of one or more sample containers 120 may be accomplished as described above. The identification apparatus 500 may function to read a barcode on the sample container 120, or determine a physical characteristic of the sample container 120 or of the specimen contained therein. A controller 551 may be used to control a speed of the moving floor 543 and belt 534. As described above, the speed information for the moving floor 543 and belt 534 may be correlated to the rotational speed 537 and translational speed 552 of the carrier 125. Thus, these speeds may be provided to the image processor 548 to assist in identifying and tracking the location of the sample container 120 in the images provided within image fields 545A, 545B.

Figure 6:
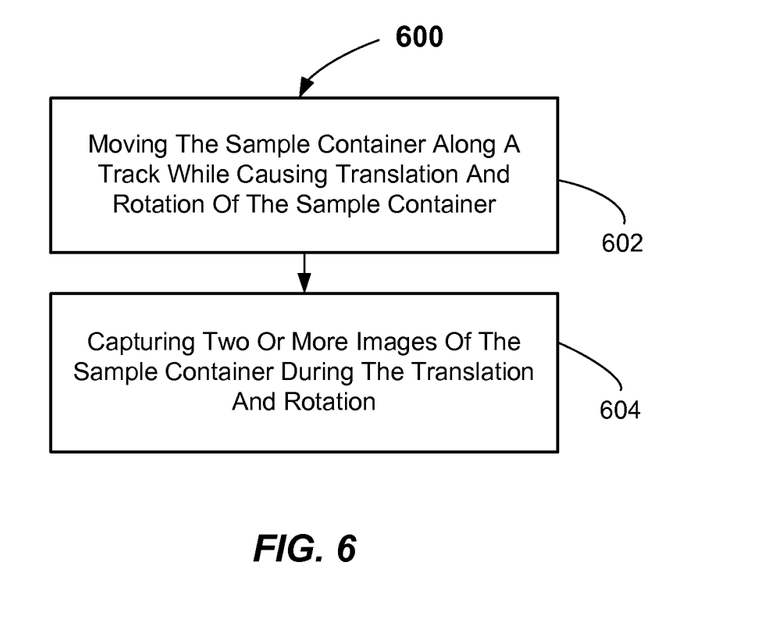
FIG. 6 is an illustration of a method of identifying according to embodiments.

According to embodiments, a method 600 of determining a characteristic of a sample container or a specimen contained within the sample container is provided. The method, as best shown in FIG. 6, includes, in 602, moving the sample container along a track (e.g., track 130, 430, 530) while causing translation and rotation of the sample container (e.g., 120), and, in 604, capturing two or more images (e.g., 365A-365D) of the sample container during the translation and rotation. In one or more embodiments, simultaneous rotation and translation may be provided. The images are taken as the sample container 120 is traversing on the track 130 such that the sample container 120 does not need to stop. In one aspect, the images may be analyzed by an image processor (e.g., 148) to read a barcode label 120D on the sample container 120. In another aspect, the images may be analyzed by an image processor (e.g., 148, 448, 548) to determine a physical characteristic of the sample container 120 such as height H, width W, capped or uncapped, cap type, and cap color. Additionally, or optionally, the images may be analyzed by an image processor (e.g., 148, 448, 548) to determine a characteristic of the specimen 120S in the sample container 120 such as overall liquid level, red blood cell portion height ($H_{RBC}$), height of the serum or plasma portion ($H_{SP}$), presence of lipemia, presence of hemolysis, and/or presence of icterus.

It should be readily appreciated by those persons skilled in the art that the present invention is susceptible of broad utility and application. Many embodiments and adaptations of the present invention other than those herein described, as well as many variations, modifications, and equivalent arrangements, will be apparent from, or reasonably suggested by, the present invention and the foregoing description thereof, without departing from the substance or scope of the present invention. For example, other types of tracks containing alternative carrier transport mechanisms that may cause the rotation and translation of the sample container 120 may be used in order to obtain images thereof. Accordingly, while the present invention has been described herein in detail in relation to specific embodiments, it is to be understood that this disclosure is only illustrative and exemplary of the present invention and is made merely for purposes of providing a full and enabling disclosure of the invention. This disclosure is not intended to limit the invention to the particular systems, apparatus, or methods disclosed, but, to the contrary, the intention is to cover all modifications, equivalents, and alternatives falling within the scope of the invention.

What is claimed is:

1. A method of determining a characteristic of a sample container or a specimen contained within the sample container, comprising:
   translating the sample container along a track while the sample container is in the field of view of an imaging apparatus;
   contacting a carrier holding the sample container between a first horizontally-movable member and a wall;
   rotating the sample container while the sample container is in the field of view of the imaging apparatus by moving the first horizontally-movable member relative to the carrier and the wall; and
   capturing two or more images of the sample container with the imaging apparatus during the translation and rotation of the sample container.

2. The method of claim 1, comprising causing simultaneous translation and rotation of the sample container while the sample container is in the field of view of the imaging apparatus.

3. The method of claim 1, comprising analyzing at least one of the two or more images to determine a presence of one or more interferents within the specimen.

4. The method of claim 3, wherein the one or more interferents comprise:
   an amount of lipemia in a serum or plasma portion of the specimen;
   an amount of hemolysis in a serum or plasma portion of the specimen; or
   an amount of icterus in a serum or plasma portion of the specimen.

5. The method of claim 1, comprising analyzing at least one of the two or more images to read a barcode on the sample container.

6. The method of claim 1, comprising analyzing at least one of the two or more images to determine a characteristic of the sample container.

7. The method of claim 1, wherein the capturing an image further comprises:
   illuminating the sample container during the translation and rotation of the sample container while the sample container is in the field of view of the imaging apparatus.

8. The method of claim 1, wherein the capturing an image further comprises:
   providing an imaging background and imaging the sample container against the imaging background during the translation and rotation.

9. The method of claim 1, wherein the first horizontally-moveable member is a first horizontally-moveable belt, and wherein the wall is a second horizontally-movable belt, and wherein rotating the sample container comprises:
   contacting a first side of a carrier holding the sample container with the first horizontally-moveable belt;
   contacting a second side of the carrier with the second horizontally-moveable belt; and
   rotating the sample container by moving the first horizontally-moveable belt and the second horizontally-moveable belt relative to the carrier.

10. The method of claim 1, wherein the wall is a stationary wall, and wherein rotating the sample container comprises:
    contacting a first side of a carrier holding the sample container with the first horizontally-moveable member;
    contacting a second side of the carrier holding the sample container with the stationary wall; and
    rotating the sample container by moving the first horizontally-moveable member relative to the stationary wall and the carrier.

11. The method of claim 1, wherein the wall is a second horizontally-movable member, and comprising contacting the carrier holding the sample container between the first horizontally-moveable member and the second horizontally-moveable member, and at least one of:
    moving the first horizontally-moveable member and the second horizontally-moveable member in opposite directions;
    moving the first horizontally-moveable member and the second horizontally-moveable member in a same direction but at different speeds;
    moving one of the first horizontally-moveable member or the second horizontally-moveable member; and
    solely translating the carrier holding the sample container at certain times, solely rotating the carrier at certain times, and rotating and translating the carrier at other times.

12. An identification apparatus, comprising:
    a track adapted to cause translation of a carrier holding a sample container containing a specimen;
    a wall adapted to contact the carrier;
    a horizontally-moveable member adapted to contact the carrier, wherein the carrier is configured to be located between the wall and the horizontally-movable member, and wherein the carrier is configured to be rotated by movement of the horizontally-moveable member relative to the carrier and the wall; and
    an imaging apparatus adapted to capture two or more images of the sample container during the translation and rotation.

13. The apparatus of claim 12, comprising an illumination source adapted to illuminate the sample container.

14. The apparatus of claim 12, comprising an imaging background, wherein the sample container is located between a camera of the imaging apparatus and the imaging background during the translation and rotation.

15. The apparatus of claim 12, comprising an image processor adapted to analyze the two or more images.

16. The apparatus of claim 15, wherein the image processor analyzes at least one of the two or more images to determine a presence of one or more interferents within the specimen.

17. The apparatus of claim 15, wherein the image processor analyzes at least one of the two or more images to read a barcode on the sample container.

18. The apparatus of claim 15, wherein the image processor analyzes at least one of the two or more images to determine a characteristic of the sample container.

19. An identification system, comprising:
    a carrier adapted to hold a sample container containing a specimen;
    a track adapted to cause translation of the carrier;

a first horizontally-moveable belt adapted to contact a vertical side of the carrier;
a second horizontally-moveable belt adapted to contact a vertical side of the carrier, wherein the carrier is adapted to be located between the first horizontally-moveable belt and the second horizontally-moveable belt, and wherein the carrier is configured to be rotated by movement of the first horizontally-moveable belt relative to the second horizontally-moveable belt; and
an imaging apparatus having an image field adapted to capture at least two images of the sample container during the translation and rotation.

* * * * *